United States Patent [19]

Jolidon et al.

[11] Patent Number: 4,946,847
[45] Date of Patent: Aug. 7, 1990

[54] QUINOLINE DERIVATIVES

[75] Inventors: Synèse Jolidon, Therwil; Rita Locher, Basel; Ivan Kompis, Oberwil, all of Switzerland; Ekkehard Weiss, Inzlingen, Fed. Rep. of Germany; Pierre-Charles Wyss, Muttenz, Switzerland

[73] Assignee: Hoffmann-La Roche Inc., Nutley, N.J.

[21] Appl. No.: 274,162

[22] Filed: Nov. 21, 1988

Related U.S. Application Data

[62] Division of Ser. No. 910,566, Sep. 22, 1986, Pat. No. 4,806,541.

[30] Foreign Application Priority Data

Sep. 24, 1985 [CH] Switzerland .................. 4120/85
Aug. 7, 1986 [CH] Switzerland .................. 3177/86

[51] Int. Cl.$^5$ .................. A61K 31/535; C07D 498/14
[52] U.S. Cl. .................. 514/229.5; 514/211; 514/215; 514/224.5; 514/250; 514/285; 540/521; 544/14; 544/99; 544/343; 544/363; 546/70; 546/156
[58] Field of Search .................. 544/99, 14, 343; 540/545, 578, 579; 546/70; 514/229.5, 224.5, 211, 215, 250, 285

[56] References Cited

U.S. PATENT DOCUMENTS

| | | | |
|---|---|---|---|
| 4,092,410 | 5/1978 | Ogata et al. | 544/99 |
| 4,528,287 | 7/1985 | Itoh et al. | 514/254 |
| 4,559,342 | 12/1985 | Petersen et al. | 514/254 |
| 4,599,334 | 7/1986 | Petersen et al. | 514/253 |
| 4,666,920 | 5/1987 | Grohe et al. | 514/312 |
| 4,689,325 | 8/1987 | Chu | 544/99 |

FOREIGN PATENT DOCUMENTS

A-0121727 10/1984 European Pat. Off. .

OTHER PUBLICATIONS

Derwent No. 85-253834 (Daiichi: Kokai 85/169475).
Derwent No. 86-058972 (Kokuriku: Kokai 86/10574).
Derwent No. 20158 E (EP 47005).
Derwent No. 49914 K (Kokai 83/62113).
Derwent No. 55216 K (Kokai 83/72589).
Derwent No. 84-020139 (Kokai 83/210092).
Derwent No. 40417 A (Kyorin: BE 863429).
Derwent No. 32008 C (Kyorin: Kokai 80/40656).
Derwent No. 70752 E (Kyorin: GB 2093018).
Derwent No. 47860 D (Kyorin: DE 887574).
Derwent No. 84-295287 (Bayer: DE 3318145).
Derwent No. 85-231535 (Abbott: EP 154780).

*Primary Examiner*—Richard L. Raymond
*Assistant Examiner*—James H. Turnipseed
*Attorney, Agent, or Firm*—George M. Gould; Bernard S. Leon; William G. Isgro

[57] ABSTRACT

Tetracyclic compounds of the formula t,10 wherein $R^1$, $R^2$, X, Y, Z and n are as hereinafter described, and salts thereof, prepared starting from corresponding tricyclic compounds, are described. The compounds I and some of the said tricyclic compounds have antibacterial activity, and are therefore useful as antibacterial agents.

10 Claims, No Drawings

QUINOLINE DERIVATIVES

This is a division of application Ser. No. 910,566 filed Sept. 22, 1986, now U.S. Pat. No. 4,806,541.

BRIEF SUMMARY OF THE INVENTION

The invention relates to quinoline derivatives of the formula

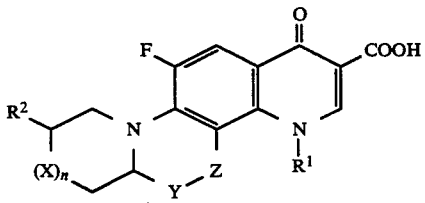

wherein
 n is the integer 1 or 0,
 X is a group N—R,
 R is hydrogen, $C_{1-4}$-alkyl, $C_{2-4}$-alkylene-$N(R^a,R^b)$ or optionally ring-substituted benzyl,
 Y is methylene or ethylene,
 Z is methylene, O or S,
 $R^1$ is $C_{3-6}$-cycloalkyl, $N(R^c,R^d)$, optionally substituted phenyl or optionally fluorinated $C_{1-4}$-alkyl or $C_{2-4}$-alkenyl,
 $R^2$ is hydrogen, $C_{1-4}$-alkyl or, when n is 0, it can also be OH or $N(R^e,R^f)$,
 $R^a$ to $R^g$ are hydrogen or $C_{1-4}$-alkyl or $N(R^a,R^b)$ is a 5- or 6-membered saturated residue optionally containing an additional heteroatom O or N—$R^g$,
and pharmaceutically acceptable salts thereof.

In another aspect, the invention relates to compounds of the formula

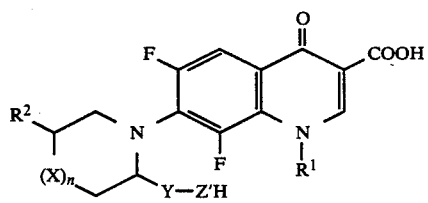

wherein $R^1$, $R^2$, X, Y, Z' and n are as herein described. The compounds of Formula I and Formula III are useful as antibacterial agents.

DETAILED DESCRIPTION OF THE INVENTION

The invention relates to quinoline derivatives, a process for their preparation, intermediates usable in the process, as well as medicaments based on the said quinoline derivatives or intermediates.

More specifically, the invention relates to quinoline derivatives of the formula

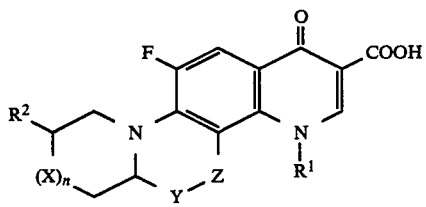

wherein
 n is the integer 1 or 0,
 X is a group N—R,
 R is hydrogen, $C_{1-4}$-alkyl, $C_{2-4}$-alkylene-$N(R^a,R^b)$ or optionally ring-substituted benzyl,
 Y is methylene or ethylene,
 Z is methylene, O or S,
 $R^1$ is $C_{3-6}$-cycloalkyl, $N(R^c,R^d)$, optionally substituted phenyl or optionally fluorinated $C_{1-4}$-alkyl or $C_{2-4}$-alkenyl,
 $R^2$ is hydrogen, $C_{1-4}$-alkyl or, when n is 0, it can also be OH or $N(R^e,R^f)$,
 $R^a$ to $R^g$ are hydrogen or $C_{1-4}$-alkyl or $N(R^a,R^b)$ is a 5- or 6-membered saturated residue optionally containing an additional heteroatom O or N—$R^g$;
and pharmaceutically acceptable salts thereof.

As used herein, $C_{1-4}$-alkyl and $C_{2-4}$-alkenyl residues, which can be straight- or branched-chain, are exemplified by methyl, ethyl, propyl, isopropyl and butyl, and allyl and vinyl, respectively. Mono- or dimethylaminoethyl are examples of aminoalkylene residues denoted by R. Pyrrolidinyl, piperidinyl, morpholinyl and piperazinyl are examples of heterocyclic residues denoted by —$N(R^a,R^b)$. Mono- and dimethylamino are examples of alkylated amino residues denoted by $R^1$ or $R^2$. 2-Fluoroethyl is an example of a fluorinated alkyl residue denoted by $R^1$. Cyclopropyl and cyclobutyl are examples of cycloalkyl residues denoted by $R^1$. The phenyl residues denoted by $R^1$ and the benzyl residues denoted by R can contain independently up to 3 substituents, such as, hydroxy; halogen, for example, fluorine or chlorine; $C_{1-4}$-alkyl, for example, methyl; $C_{1-4}$-alkoxy, for example, methoxy; or nitro.

The pharmaceutically acceptable salts of the compounds of formula I can be physiologically compatible alkali metal, alkaline earth metal and optionally substituted ammonium salts, as well as addition salts with physiologically compatible strong inorganic and organic acids, for example, hydrochloric acid, sulfuric acid, phosphoric acid, methanesulfonic acid or p-toluenesulfonic acid or the like.

The quinoline derivatives of formulas I and III, in accordance with the invention, contain at least one asymmetric C-atom and can therefore exist as enantiomers, as diastereomers or as mixtures, for example, as racemates.

The compounds of formula I can be prepared in a known manner by
 (a) saponifying a lower alkyl ester corresponding to the acid of formula I, or
 (b) cleaving nitrogen protecting groups which may be present in an acid of the formula

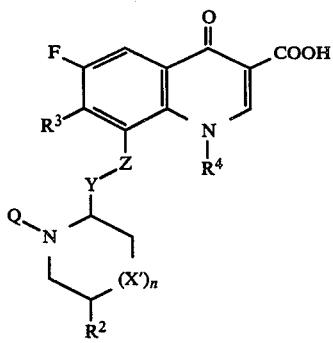

wherein X' is a group N—R of N—Q', Q and Q' are hydrogen or a nitrogen protecting group, $R^3$ is halogen, and $R^4$ is hydrogen or $R^4$ has the same significance as $R^1$, and $R^1$, $R^2$, R, Y, Z and n are as previously described, and cyclizing the resulting secondary amine, or (c) cyclizing an acid of the formula

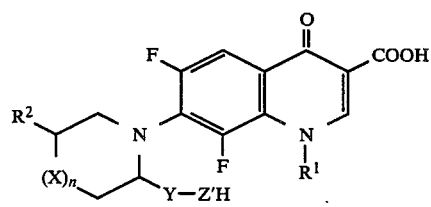

wherein Z' is oxygen or sulfur and n, X, Y, $R^1$ and $R^2$ are as previously described (d) if desired, reacting a compound of formula I obtained with an agent which introduces the group R or the group $R^1$, (e) if desired, converting the hydroxy group $R^2$ in a compound of formula I obtained into an amino group $N(R^e, R^f)$, (f) if desired, converting the vinyl residue $R^1$ in a compound of formula I obtained into a cyclopropyl residue, (g) if desired, isolating an acid obtained in the form of a salt.

In the saponification, process ovariant (a), the ethyl ester corresponding to the acid of formula I is conveniently reacted with a base, for example, an inorganic base such as an alkali metal or alkaline earth metal hydroxide or carbonate, in a solvent, for example, a lower alkanol such as ethanol, while heating, for example, up to the reflux temperature of the reaction mixture.

The nitrogen protecting groups Q or Q' in the acid starting materials of formula II can be, for example, benzyl and p-nitro-benzyl. Fluorine and chlorine are preferred as the halogen denoted by $R^3$. Process variant (b) can be carried out by firstly cleaving off hydrogenolytically any nitrogen protecting groups Q or Q' and then cyclizing the resulting secondary amine conveniently in situ by an intramolecular nucleophilic substitution reaction. The hydrogenolytic cleavage of protecting groups can be carried out in the presence of a hydrogenation catalyst such as palladium-on-carbon (Pd/C) in acidic medium, for example, in glacial acetic acid. When $R^3$ is fluorine, the subsequent cyclization can be carried out in a solvent such as acetonitrile at a temperature up to the reflux temperature, for example, at 50°-60° C. When $R^3$ is chlorine, the cyclization is conveniently carried out in a solvent such as pyridine at a temperature up to the reflux temperature, for example, at 50°-80° C.

The cyclization, process variant (c), can be carried out in a solvent such as dimethylformamide (DMF) or dimethyl sulfoxide (DMSO) in the presence of base such as sodium hydride while heating at a temperature up to the reflux temperature, for example, at 130°-140° C.

As agents which introduce the group R or $R^1$, halides such as iodides, for example, ethyl iodide; mesylates or tosylates, can be used. Process variant (d) can be carried out, if desired with intermediary protection of one of the two N-atoms to be substituted, for example, with one of the nitrogen protecting groups mentioned above, in a solvent such as DMF, in the presence of a base, for example, an inorganic base such as an alkali metal or alkaline earth metal hydroxide or carbonate, for example potassium carbonate, while heating, for example, to 80° C.

The conversion, in process variant (e) can be carried out by firstly esterifying an alcohol of formula I in which $R^2$ is hydroxy, for example, with p-tosyl chloride or mesyl chloride, in a solvent such as methylene chloride, dioxane or tetrahydrofuran (THF) in the presence of a base such as triethylamine at room temperature, and then reacting the tosylate or mesylate obtained with an excess of an amine $HN(R^e, R^f)$ in a solvent such as THF, dioxan or DMSO at a temperature up to about 100° C. Alternatively, an alcohol of formula I can be oxidized to the corresponding ketone, for example, by means of Jones reagent ($CrO_3/H_2SO_4$) in acetone at 20°-35° C., and the ketone can then be reacted with the amine $HN(R^e, R^f)$, optionally in the presence of a molecular sieve, in a solvent such as THF or dioxane at room temperature and the product obtained can be subsequently reduced, for example, with sodium borohydride in ethanol at 20°-60° C. or with formic acid according to Leuckart-Wallach (Org. Reactions 5, 1949, 301). The ketone corresponding to the alcohol I can also be converted with phenylhydrazone in a solvent such as an alcohol, for example, ethanol, at room temperature into the corresponding phenylhydrazide. The latter can then be converted into the amine of formula I in which $R^2$ is amino with a reducing agent such as sodium amalgam in the aforementioned solvent while heating to the reflux temperature.

The conversion, in process variant, (f) can be carried out according to the method of Simmons-Smith by means of iodomethyl zinc iodide or by reacting the enamine of formula I with diazomethane in the presence of copper(I) chloride.

The lower alkyl esters used in process variant (a) can be prepared from the lower alkyl esters corresponding to the acids of formula II, for example, as described above for process variant (b). If desired, such esters which are unsubstituted on one (or on both) N-atom(s) can be reacted with an agent which introduces one of the groups R (or $R^1$), for example, as described above for process variant (d).

The acids of formulas II and III can be prepared by saponifying the corresponding lower alkyl esters, for example, in analogy to process variant (a). The aforementioned acid and ester starting materials also form part of the invention. They can be prepared in a known manner, especially in the manner described hereinafter or in analogy thereto.

Thus, the acids of formula II in which $R^4$ is hydrogen can be prepared starting from the compounds of the formula

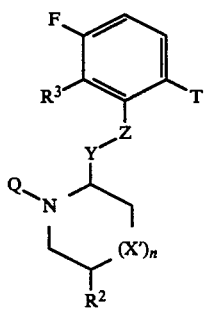

IV wherein T is nitro, amino or 2-bis(carbo-$C_{1-4}$-alkoxy)-vinylamino and n, Q, $R^2$, $R^3$, X', Y and Z are as previously described.

The reduction of the nitro group T to the amino group T can be carried out, for example, with zinc dust in acetic acid. An amine IV obtained can be converted by heating, for example, to 110° C., with a di-$C_{1-4}$-alkyl $C_{1-4}$-alkoxymethylenemalonate, for example, with diethyl ethoxymethylenemalonate, into the corresponding vinylamine IV. The latter can be cyclized to a $C_{1-4}$-alkyl ester corresponding to the acid of formula II in which $R^4$ is hydrogen, for example, with ethyl polyphosphate under an inert atmosphere and at elevated temperature, for example, under $N_2$ at 100° C.

The compounds IV when T is nitro can be prepared in a knwon manner. Thus, a compound IV when Z is oxygen or sulfur can be prepared by reacting a nitrobenzene derivative of formula V with a piperazine or pyrrolidine derivative of formula VI,

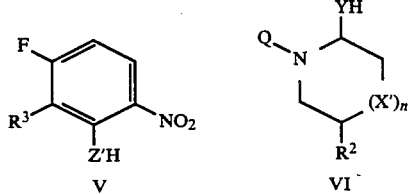

wherein n, Z', Q, $R^2$, $R^3$, X' and Y are as previously described, for example, in the presence of triphenylphosphine and diethyl diazadicarboxylate in a solvent such as THF.

As mentioned above, the acids of formula III can be prepared by saponifying the corresponding lower alkyl esters. The latter can be prepared by the nucleophilic substitution of an ester of formula VII with an amine of formula VIII

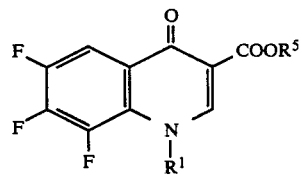

VII

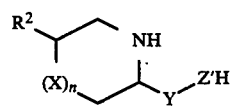

VIII wherein $R^5$ is lower-alkyl and n, $R^1$, $R^2$, Y and Z' are as previously described, in a solvent such as N-methylpyrrolidine or c-picoline while heating, for example, to 80° C.

The trifluorinated quinoline derivatives of formula VII can be prepared by reacting the corresponding tetrafluorinated benzene derivative of the formula

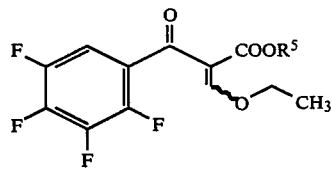

IX with an amine $R^1$—$NH_2$ in a solvent such as methylene chloride, ethanol or chloroform. When $R^1$ is a primary or secondary amino group, the N-atom thereof must be intermediately protected, for example, with a dimethyl-t-butyl-silyl group.

The compounds of formulas V to IX are known or can be prepared in a known manner.

Among the compounds of formulas I and II, preferred are those in which n is the integer 1, R is hydrogen, $C_{1-4}$-alkyl or $C_{2-4}$-alkylene-$N(R^a,R^b)$ and $R^2$ is hydrogen. Among the compounds of formulas I, II and III, preferred are those in which R is hydrogen, $C_{1-4}$-alkyl, especially methyl or ethyl, or ring-substituted benzyl, especially p-nitrobenzyl; and/or in which Y is methylene and Z or Z' is oxygen; and/or in which $R^1$ or $R^4$ is hydrogen, optionally fluorinated $C_{1-4}$-alkyl, especially methyl, ethyl or 2-fluoroethyl, $C_{3-6}$-cycloalkyl, especially cyclopropyl; $N(R^c,R^d)$, especially methylamino, or substituted phenyl, especially p-fluorophenyl. The compounds of formulas I, II and III in which $R^2$ is hydrogen or hydroxy; and/or in which R is hydrogen or methyl; and/or in which $R^1$ or $R^4$ is ethyl, cyclopropyl or methylamino are especially preferred.

Examples of preferred compounds are
1-cyclopropyl-6,8-difluoro-1,4-dihydro-7-(2-hydroxymethyl-4-methyl-1-piperazinyl)-4-oxoquinoline-3-carboxylic acid,
1-ethyl-6-fluoro-1,4,8,9,10,11,11a,12-octahydro-10-methyl-4-oxopyrazino[1',2':4,5][1,4]oxazino[3,2-h]quinoline-3-carboxylic acid and
1-ethyl-6-fluoro-1,4,8,9,10,11,11a,12-octahydro-4-oxopyrazino[1',2':4,5][1,4]oxazino[3,2-h]quinoline-3-carboxylic acid.

Further examples of compounds of formulas I or III are
1-cyclopropyl-6-fluoro-1,4,8,9,10,11,11a,12-octahydro-4-oxopyrazino[1',2':4,5][1,4]oxazino[3,2-h]quinoline-3-carboxylic acid,
1-cyclopropyl-6-fluoro-10-methyl-1,4,8,9,10,11,11a,12-octahydro-4-oxopyrazino[1',2':4,5][1,4]oxazino[3,2-h]quinoline-3-carboxylic acid,
6-fluoro-1-(p-fluorophenyl)-1,4,8,9,10,11,11a,12-octahydro-4-oxopyrazino[1',2':4,5][1,4]oxazino[3,2-h]quinoline-3-carboxylic acid, 6-fluoro-1-(p-fluorophenyl)-10-methyl-1,4,8,9,10,11,11a,12-octahydro-4-oxopyrazino[1',2':4,5][1,4]oxazino[3,2-h]quinoline-3-carboxylic acid, 6-fluoro-1-(2-fluoroethyl)-1,4,8,9,10,11,11a,12-octahydro-4-oxopyrazino[1',2':4,5][1,4]oxazino[3,2-h]quinoline-3-carboxylic acid, 6-fluoro-1-(2-fluoroethyl)-10-methyl-1,4,8,9,10,11,11a,12-octahydro-4-oxopyrazino[1',2':4,5][1,4]oxazino[3,2-h]quinoline-3-carboxylic acid, 6-fluoro-1-methylamino-1,4,8,9,10,11,11a,12-octahydro-4-oxopyrazino[1',2':4,5][1,4]oxazino[3,2-h]quinoline-3-carboxylic acid, 6-fluoro-10-methyl-1-methylamino-1,4,8,9,10,11,11a,12-octahydro-4-oxopyrazino[1',2':4,5][1,4]oxazino[3,2-h]quinoline-3-carboxylic acid, (S)-4-ethyl-11-fluoro-1,4,6a,7,8,9-hexahydro-1-oxo-6H-pyrrolo[1',2':4,5][1,4]oxazino[3,2-h]quinoline-2-carboxylic acid, 6a(S),8(S)-4-ethyl-11-fluoro-1,4,6a,7,8,9-hexahydro-8-hydroxy-1-oxo-6H-pyrrolo[1',2':4,5][1,4]oxazino[3,2-h]quinoline-2-carboxylic acid, 6a(S)-8-amino-4-ethyl-11-fluoro-1,4,6a,7,8,9a-hexahydro-1-oxo-6H-pyrrolo[1',2':4,5][1,4]oxazino[3,2-h]quinoline-2-carboxylic acid, 6a(S)-8-amino-4-cyclopropyl-11-fluoro-1,4,6a,7,8,9-hexahydro-1-oxo-6H-pyrrolo[1',2':4,5][1,4]oxazino[3,2-h]quinoline-2-carboxylic acid, 6a(S),8(S)-11-fluoro-4-(p-fluorophenyl)-1,4,6a,7,8,9-hexahydro-8-hydroxy-1-oxo-6H-pyrrolo[1',2':4,5]oxazino[3,2-h]quinoline-2-carboxylic acid, 6a(S)-8-amino-11-fluoro-4-(p-fluorophenyl)-1,4,6a,7,8,9-hexahydro-1-oxo-6H-pyrrolo[1',2':4,5][1,4]oxazino[3,2-h]quinoline-2-carboxylic acid, 6a(S), 8(S)-11-fluoro-1,4,6a,7,8,9-hexahydro-8-hydroxy-4-methylamino-1-oxo-6H-pyrrolo[1',2':4,5][1,4]oxazino[3,2-h]quinoline-2-carboxylic acid, 6a(S)-8-amino-11-fluoro-1,4,6a,7,8,9-hexahydro-4-methylamino-1-oxo-6H-pyrrolo[1',2':4,5][1,4]oxazino[3,2-h]quinoline-2-carboxylic acid, 1-ethyl-6,8-difluoro-1,4-dihydro-7-(2-hydroxymethyl-1-piperazinyl)-4-oxoquinoline-3-carboxylic acid, 1-ethyl-6,8-difluoro-1,4-dihydro-7-(2-hydroxymethyl-4-methyl-1-piperazinyl)-4-oxoquinoline-3-carboxylic acid, 1-cyclopropyl-6,8-difluoro-1,4-dihydro-7-(2-hydroxymethyl-1-piperazinyl)-4-oxoquinoline-3-carboxylic acid, 6,8-difluoro-1,4-dihydro-1-(p-fluorophenyl)-7-(2-hydroxymethyl-1-piperazinyl)-4-oxoquinoline-3-carboxylic acid, 6,8-difluoro-1,4-dihydro-1-(2-fluoroethyl)-7-(2-hydroxymethyl-1-piperazinyl)-4-oxoquinoline-3-carboxylic acid and 6,8-difluoro-1,4-dihydro-1-methylamino-7-(2-hydroxymethyl-1-piperazinyl)-4-oxoquinoline-3-carboxylic acid.

The quinoline derivatives of formulas I and III, in accordance with the invention, are pharmacologically active. They possess antibacterial activity and are characterized by low acute toxicities. Therefore, they are useful as antibacterial agents. They are active, for example, against gram-positive aerobic bacteria such as *S. aureus, S. pyogenes, S. faecalis* or *S. pneumoniae,* against Enterobacteriaceae such as *E. coli* or *E. cloacae,* against *P. aeruginosa* and *A. anitratus.* Thus, the minimal inhibitory concentrations in µg/ml given hereinafter for the following compounds were determined against some of these organisms.

Compound A (Example 1)

1-Ethyl-6-fluoro-1,4,8,9,10,11,11a,12-octahydro-4-oxopyrazino[1',2':4,5][1,4]oxazino[3,2-h]quinoline-3-carboxylic acid

Compound B (Example 8a)

1-Cyclopropyl-6,8-difluoro-1,4-dihydro-7-(2-hydroxymethyl-4-methyl-1-piperazinyl)-4-oxoquinoline-3-carboxylic acid

Compound C (Example 2A)

1-Ethyl-6-fluoro-1,4,8,9,10,11,11a,12-octahydro-10-methyl-4-oxopyrazino[1',2':4,5][1,4]oxazino[3,2-h]quinoline-3-carboxylic acid

Compound D (Example 8c)

6,8-Difluoro-1,4-dihydro-1-(p-fluorophenyl)-7-(2-hydroxymethyl-4-methyl-1-piperazinyl)-4-oxoquinoline-3-carboxylic acid

Compound E (Example 4A)

(S)-4-Cyclopropyl-11-fluoro-1,4,6a,7,8,9-hexahydro-1-oxo-6H-pyrrolo[1',2':4,5][1,4]oxazino[3,2-h]quinoline-2-carboxylic acid

Compound F (Example 3a)

1,10-Diethyl-6-fluoro-1,4,8,9,10,11,11a,12-octahydro-4-oxopyrazino[1',2':4,5][1,4]oxazino[3,2-h]quinoline-3-carboxylic acid.

|  | A | B | C | D | E | F |
|---|---|---|---|---|---|---|
| *E. coli* 1346 | <0.12 | 0.06 | 0.25 | 0.5 | 1 | 0.5 |
| *E. coli* 25922 | 0.25 | 0.06 | 0.25 | 0.25 | 0.5 | 0.5 |
| *E. coli* 1527E | <0.12 | 0.03 | <0.03 | 0.03 | 0.03 | 0.12 |
| *E. cloacae* P99 | <0.12 | 0.06 | 0.12 | 0.25 | 0.25 | 0.5 |
| *S. aureus* 25923 |  | 0.5 | 1 | 1 | 0.12 | 2 |
| *S. aureus* 887 | 1 | 0.5 | 1 | 1 | 0.12 | 2 |
| *S. aureus* 743 |  | 0.5 | 1 | 1 | 0.12 | 2 |
| *S. faecalis* 6 | 8 | 2 | 32 | 4 | 2 | 16 |
| *S. pyogenes* β15 | 2 | 2 | 32 | 4 | 1 | 32 |
| *S. pneumoniae* BA | 2 | 2 | 32 | 2 | 1 | 16 |
| *A. anitratus* 5I-156 | 1 | 0.25 | 0.25 | 1 | 2 | 1 |

The quinoline derivatives of formulas I and III, in accordance with the invention, can be used in the therapy and prophylaxis of diseases, especially of bacterial infections, in the form of pharmaceutical preparations with direct or delayed liberation of the active substance in admixture with an organic or inorganic inert carrier material which is suitable for oral, rectal or parenteral administration, for example, water, gelatine, gum arabic, lactose, starch, magnesium stearate, talc, vegetable oils, polyalkylene glycols and the like. The pharmaceutical preparations can be present in solid form, for example, as tablets, dragees, suppositories, capsules; in semi-solid form, for example, as salves; or in liquid form, for example, as solutions, suspensions or emulsions. If desired, they are sterilized and/or contain further adjuvants such as preserving, stabilizing, wetting or emulsifying agents, flavor-improving agents, salts for varying the osmotic pressure or buffer substances.

The preparation of the pharmaceutical compositions can be effected in a manner which is familiar to a person skilled in the art, namely by mixing the active substance with non-toxic, inert carrier materials suitable for therapeutic administration and bringing the mixture obtained into the suitable galenical form.

An amount in the range of from about 10 μg to 100 mg/kg, preferably about 4 mg/kg, body weight per day can be regarded as a dosage guideline for a compound of formula I or III.

EXAMPLE 1

(1A) A solution of 0.165 g (0.44 mmol) of ethyl 1-ethyl-6-fluoro-1,4,8,9,10,11,11a,12-octahydro-4-oxopyrazino-[1',2':4,5][1,4]-oxazino[3,2-h]quinoline-3-carboxylate in 10 ml of ethanol and 7.5 ml of 0.1N sodium hydroxide was stirred at 70° C. for 90 minutes. The solution was neutralized with 7.5 ml of 0.1N hydrochloric acid. Ethanol was removed under reduced pressure and the solid product was filtered off, washed and dried. There were obtained 120 mg of 1-ethyl-6-fluoro-1,4,8,9,10,11,11a,12-octahydro-4-oxopyrazino-[1',2':4,5][1,4]-oxazino[3,2-h]quinoline-3-carboxylic acid, m.p. 266°–268° C.

(1B) The ester starting material can be prepared as follows:

(1Ba) A solution of 4.7 g (27 mmol) of diethyl azodicarboxylate in 15 ml of THF was added dropwise at 15° C. while stirring to a solution of 3.9 g (22.5 mmol) of 2,3-difluoro-5-nitrophenol, 7.1 g (27 mmol) of triphenylphosphine and 8 g (0.27 mmol) of 1,4-dibenzyl-2-hydroxymethylpiperazine in 250 ml of THF. The yellow reaction solution was then stirred at room temperature for an additional 3 hours. After concentrating the reaction solution, the oily residue was stirred with a total of 2 l of hot n-hexane in several portions. The hexane solution was separated and cooled. The separated triphenylphosphine oxide was removed by filtration under suction, and the filtrate was concentrated. Chromatography on silica gel with ether/n-hexane (1:1) as the eluent gave 7.4 g of 1,4-dibenzyl-2-[(6-nitro-2,3-difluorophenoxy)methyl]-piperazine as a brown oil.

(1Bb) 19 g (0.29 g atom) of zinc dust were introduced in portions while stirring at room temperature into a solution of 7.1 g (15.7 mmol) of the product of (1Ba) in 108 ml of glacial acetic acid and 36 ml of water. The temperature rose to 40° C. The mixture was then stirred at 50° C. for 1 hour and the warm suspension was suction filtered. The cooled filtrate was treated with 300 ml of ether. The white precipitate was separated and discarded and the solution was evaporated to dryness. The oily residue was taken up in water, adjusted to pH 5 with concentrated sodium hydroxide and extracted with ether. The ether phases were washed in succession with 5% sodium bicarbonate and water, dried and concentrated. The residual oil was purified on silica gel with ether/n-hexane (1:1) and gave 6.0 g of 1,4-dibenzyl-2-[(6-amino-2,3-difluorophenoxy)methyl]piperazine as a brownish oil.

(1Bc) Ethanol was distilled at 110° C. bath temperature during 40 minutes from a mixture of 4.3 g (10.2 mmol) of the product of (1Bb) and 2.4 g (11.2 mmol) of diethyl ethoxymethylenemalonate. The reaction mixture was cooled. Recrystallization from ethanol gave 5.0 g of diethyl 2-[(1,4-dibenzyl-2-piperazinyl)methoxy]-3,4-difluoroanilino]methylenemalonate, m.p. 109°–110° C.

(1Bd) A mixture of 4.4 g (7.41 mmol) of the product of (1Bc) and 30 g of ethyl polyphosphate was stirred at 100° C. under nitrogen gasification for 10 hours. The mixture was mixed with ice/water while cooling and adjusted to pH 8 with 4N sodium hydroxide. The solid product was filtered under suction and crystallized from ethyl acetate n-hexane. There was obtained [-[(1,4-dibenzyl-2-piperazinyl)-methoxy]-6,7-difluoro-1,4-dihydro-4-oxoquinoline-3-carboxylic acid, m.p. 158°–159° C.

(1Be) A suspension of 1.38 g (2.4 mmol) of the product of (1Bd), 0.85 g of potassium carbonate and 1.94 g (12 mmol) of ethyl iodide in 14 ml of DMF was stirred at 80° C. for 2.5 hours. The inorganic salts were removed by filtration under suction, the filtrate was concentrated and the evaporation residue was stirred with ether. The solution was concentrated and the residue was chromatographed on silica gel with ethyl acetate/n-hexane (3:1). Crystallization from ether/petroleum ether gave ethyl [-[(1,4-dibenzyl-2-piperazinyl)-methoxy]-6,7-difluoro-1-ethyl-1,4-dihydro-4-oxoquinoline-3-carboxylate, m.p. 121°–122° C.

(1Bf) A suspension of 0.5 g (0.86 mmol) of the product of (1Be) and 0.5 g of 5% Pd/C in 10 ml of glacial acetic acid was hydrogenated at 25° C. for 240 minutes under a hydrogen pressure of 10 bar. The catalyst was removed by filtration under suction and rinsed with 10 ml of glacial acetic acid. The solvent was then removed at 25° C. under 0.4 mba. The residue was taken up in 10 ml of acetonitrile and boiled at reflux for 45 minutes. The resulting suspension was cooled to 0° C. and suction filtered. The solid product was dissolved in 2 ml of water and the solution was adjusted to pH 8 with 0.1N sodium hydroxide. The separated product was removed by filtration under suction, washed and dried. There was obtained ethyl 1-ethyl-6-fluoro-1,4,8,9,10,11,11a,12-octahydro-4-oxopyrazino[1',2':4,5][1,4]oxazino[3,2-h]quinoline-3-carboxylate, m.p. 266°–268° C.

EXAMPLE 2

(2A) A solution of 0.24 g (0.61 mmol) of ethyl 1-ethyl-6-fluoro-1,4,8,9,10,11,11a,12-octahydro-10-methyl-4-oxopyrazino[1',2':4,5][1,4]oxazino[3,2-h]quinoline-3-carboxylate in 15 ml of ethanol and 6.8 ml of 0.1N sodium hydroxide was stirred at 85° C. for 1 hour. The reaction solution was neutralized with 6.8 ml of 0.1N hydrochloric acid and evaporated, and the solid product was removed by filtration under suction. Crystallization from ethanol gave 1-ethyl-6-fluoro-1,4,8,9,10,11,11a,12-octahydro-10-methyl-4-oxopyrazino-[1',2':4,5][1,4]oxazino[3,2-h]quinoline-3-carboxylic acid, m.p. >270° C.

(2B) The ester starting material can be prepared as follows:

0.33 g (24 mmol) of anhydrous potassium carbonate and 0.34 g (24 mmol) of methyl iodide were added to a solution of 0.6 g (16 mmol) of ethyl 1-ethyl-6-fluoro-1,4,8,9,10,11,11a,12-octahydro-4-oxopyrazino[1',2':4,5][1,4]oxazino[3,2-h]quinoline-3-carboxylate (Example 1Bf) in 40 ml of acetone. The suspension was stirred at room temperature for 90 minutes. The reaction mixture was filtered and the filtrate was concentrated. The residue was purified and, after recrystallization, gave ethyl 1-ethyl-6-fluoro-1,4,8,9,10,11,11a,12-octahydro-10-methyl-4-oxopyrazino[1',2':4,5][1,4]oxazino[3,2-h]quinoline-3-carboxylate, m.p. 191°–192° C.

EXAMPLE 3

Analogously to Example 2, (3a) from ethyl 1,10-diethyl-6-fluoro-1,4,8,9,10,11,11a,12-octahydro-4-oxopyrazino[1',2':4,5][1,4]oxazino[3,2-h]quinoline-3-carboxylate, m.p. 184°–186° C., there was obtained 1,10-diethyl-6-fluoro-1,4,8,9,10,11,11a,12-octahydro-4-oxopyrazino[1',2':4,5][1,4]oxazino[3,2-h]quinoline-3-carboxylic acid, m.p. 261°–264° C., and (3b) from ethyl 1-ethyl-6-fluoro-1,4,8,9,10,11a,12-octahydro-10-(p-nitrobenzyl)-4-oxopyrazino[1',2':4,5][1,4]oxazino[3,2-h]quinoline-3-carboxylate, m.p. 182°–183° C., there was obtained 1-ethyl-6-fluoro-1,4,8,9,10,11,11a,12-octahydro-10-(p-nitrobenzyl)-4-oxopyrazino[1',2':4,5][oxazino[3,2-h]quinoline-3-carboxylic acid, m.p. 240°–243° C.

EXAMPLE 4

(4A) 9.2 mg of a 55% sodium hydride dispersion were added to a solution of 0.364 g (1 mmol) of 1-cyclopropyl-6,8-difluoro-1,4-dihydro-7-[(S)-2-hydroxymethyl-1-pyrrolidinyl]-4-oxoquinoline-3-carboxylic acid in 8 ml of DMF. After completion of the hydrogen evolution, the mixture was stirred at 140° C. for 35 minutes, the solvent was evaporated, the residue was taken up in water, adjusted to pH 6 with glacial acetic acid and suction filtered. Crystallization from ethanol gave (S)-4-cyclopropyl-11-fluoro-1,4,6a,7,8,9-hexahydro-1-oxo-6H-pyrrolo[1',2':4,5][1,4]oxazino[3,2-h]quinoline-2-carboxylic acid, m.p. >275° C. (dec.), MS: 344 (M+, 58%), 300 (100), 271 (12), 245 (8), 216 (17), 189 (4), 158 (4), 41 (24).

(4B) The starting material can be prepared as follows:

A solution of 3.1 g (0.01 mmol) of ethyl 1-cyclopropyl-1,4-dihydro-4-oxo-6,7,8-trifluoroquinoline-3-carboxylate and 3.03 g (0.03 mmol) of L-prolinol in 15 ml of N-methylpyrrolidine was stirred at 80° C. for 2.5 hours. The solvent was removed by distillation under reduced pressure and the oily residue was recrystallized from ethyl acetate/ether. The resulting ester was saponified analogously to Example 1A. There was obtained 1-cyclopropyl-6,8-difluoro-1,4-dihydro-7-[(S)-2-hydroxymethyl-1-pyrrolidinyl]-4-oxoquinoline-3-carboxylic acid, m.p. 209°–210° C.

EXAMPLE 5

Analogously to Example 4, but using 3-hydroxy-L-prolinol in place of L-prolinol, there was obtained, via 1-cyclopropyl-6,8-difluoro-1,4-dihydro-7-[2(S),4(S)-4-hydroxy-2-hydroxymethyl-1-pyrrolidinyl]-4-oxoquinoline-3-carboxylic acid, m.p. 250° C. (decomposition), 6a(S),8(S)-4-cyclopropyl-11-fluoro-1,4,6a,7,8,9-hexahydro-8-hydroxy-1-oxo-6H-pyrrolo[1',2':4,5][1,4]oxazino[3,2-h]quinoline-2-carboxylic acid, m.p. 22 270° C. (decomposition). MS: 360 (M+, 30%), 316 (100), 267 (13), 247 (8), 245 (8), 217 (8), 101 (13).

EXAMPLE 6

Analogously to Example 4, (6a) from ethyl 1,4-dihydro-1-(p-fluorophenyl)-4-oxo-6,7,8-trifluoroquinoline-3-carboxylate there was obtained, via 6,8-difluoro-1,4-dihydro-1-(p-fluorophenyl)-7-[(S)-2-hydroxymethyl-1-pyrrolidinyl]-4-oxoquinoline-3-carboxylic acid, m.p. 275°–277° C. (decomposition), (S)-11-fluoro-4-(p-fluorophenyl)-1,4,6a,7,8,9-hexahydro-1-oxo-6H-pyrrolo[1',2':4,5][1,4]oxazino[3,2-h]quinoline-2-carboxylic acid, m.p. >280° C. (decomposition), MS: 398 (M+, 26%), 354 (100), 332 (10), 313 (6), 299 (6), 245 (20), 95 (12), (6b) from ethyl 1,4-dihydro-1-methylamino-4-oxo-6,7,8-trifluoroquinoline-3-carboxylate there was obtained, via 6,8-difluoro-1,4-dihydro-7-[(S)-2-hydroxymethyl-1-pyrrolidinyl]-1-methylamino-4-oxoquinoline-3-carboxylic acid, m.p. 179°–181° C.

(S)-11-fluoro-1,4,6a,7,8,9-hexahydro-4-methylamino-1-oxo-6H-pyrrolo[1',2':4,5][1,4]oxazino[3,2-h]quinoline-2-carboxylic acid, MS: 333 (M+, 72%), 289 (100), 272 (64), 260 (98), 234 (18), 231 (46), 205 (12), 191 (12), 135 (9), 41 (44), and (6c) from ethyl 1,4-dihydro-1-(2-fluoroethyl)-4-oxo-6,7,8-trifluoroquinoline-3-carboxylate there was obtained, via 6,8-difluoro-1,4-dihydro-1-(2-fluoroethyl)-7-[(S)-2-hydroxymethyl-1-pyrrolidinyl]-4-oxoquinoline-3-carboxylic acid, m.p. 195°–197° C.

(S)-11-fluoro-4-(2-fluoroethyl)-1,4,6a,7,8,9-hexahydro-1-oxo-6H-pyrrolo[1',2':4,5][1,4]oxazino[3,2-h]quinoline-2-carboxylic acid, MS: 350 (M+, 42%), 306 (100), 286 (18), 273 (18), 245 (10), 153 (12), 41 (21).

EXAMPLE 7

Analogously to Example 1, from 8-[(1,4-dibenzyl-2-piperazinyl)methoxy]-6,7-difluoro-1,4-dihydro-4-oxoquinoline-3-carboxylic acid (Example 1Bd) there was obtained using methyl iodide in place of ethyl iodide (Example 1Be)

6-fluoro-1,4,8,9,10,11,1a,12-octahydro-1-methyl-4-oxopyrazino[1',2':4,5][1,4]oxazino[3,2-h]quinoline-3-carboxylic acid, m.p. 236°–240° C. (decomposition).

EXAMPLE 8

The following compounds were obtained analogously to Example 4B using 4-methyl-2-piperazinylmethanol in place of L-prolinol:

(a) 1-Cyclopropyl-6,8-difluoro-1,4-dihydro-7-(2-hydroxymethyl-4-methyl-1-piperazinyl)-4-oxoquinoline-3-carboxylic acid, m.p. 213°–214° C., (b) 6,8-difluoro-1,4-dihydro-1-(2-fluoroethyl)-7-(2-hydroxymethyl-4-methyl-1-piperazinyl)-4-oxoquinoline-3-carboxylic acid, m.p. of the dihydrochloride >260° C. (decomposition), (c) 6,8-difluoro-1,4-dihydro-1-(p-fluorophenyl)-7-(2-hydroxymethyl-4-methyl-1-piperazinyl)-4-oxoquinoline-3-carboxylic acid, m.p. 265°–267° C., and (d) 6,8-difluoro-1,4-dihydro-7-(2-hydroxymethyl-4-methyl-1-piperazinyl)-1-methylamino-4-oxoquinoline-3-carboxylic acid, MS: 400 [(M+H)+, 1%], 368 (76), 324 (24), 309 (10), 281 (16), 70 (100), 36 (40).

EXAMPLE 9

Tablets of the following composition are prepared in the usual manner:

| Active substance | 100 | 200 | 400 mg |
|---|---|---|---|
| Powdered lactose | 25 | 70 | 200 |
| Microcrystalline cellulose | 70 | 70 | 100 |
| Maize starch | 30 | 60 | 50 |
| Polyvinylpyrrolidone | 10 | 20 | 30 |
| Sodium carboxymethyl starch | 10 | 20 | 30 |
| Talc | 3 | 8 | 16 |
| Magnesium stearate | 2 | 2 | 4 |
| | 250 | 450 | 830 mg |

We claim:

1. A compound of the formula

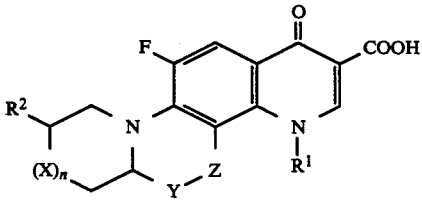

wherein
n is the integer 1 or 0,
X is a group N—R,
R is a hydrogen, $C_{1-4}$-alkyl, $C_{2-4}$-alkylene-N($R^a$, $R^b$), benzyl or benzyl independently ring-substituted by up to 3 substituents selected from the group consisting of hydroxy, halogen, $C_{1-4}$-alkyl, $C_{1-4}$-alkoxy or nitro,
Y is methylene or ethylene,
Z is methylene, O or S,
$R^1$ is $C_{3-6}$-cycloalkyl, N($R^c$, $R^d$), phenyl or phenyl independently substituted by up to 3 substituents selected from the group consisting of hydroxy, halogen, $C_{1-4}$-alkyl, $C_{1-4}$-alkoxy or nitro; or optionally fluorinated $C_{1-4}$-alkyl or $C_{2-4}$-alkenyl,
$R^2$ is hydrogen, $C_{1-4}$-alkyl or, when n is 0, it can also be OH or N($R^e$, $R^f$),
$R^a$ to $R^g$ are hydrogen or $C_{1-4}$-alkyl or N($R^a$, $R^b$) is a 5- or 6-membered saturated ring which can contain an additional heteroatom selected from O or N—$R^g$,
an enantiomer or diastereomer thereof, or pharmaceutically acceptable salt thereof.

2. A compound, in accordance with claim 1, wherein n is the integer 1, R is hydrogen, $C_{1-4}$-alkyl or $C_{2-4}$-alkylene-N($R^a$,$R^b$) and $R^2$ is hydrogen.

3. A compound, in accordance with claim 1, 1-ethyl-6-fluoro-1,4,8,9,10,11,11a,12-octahydro-10-methyl-4-oxopyrazino[1',2':4,5][1,4]oxazino[3,2-h]quinoline-3-carboxylic acid.

4. A compound, in accordance with claim 1, 1-ethyl-6-fluoro-1,4,8,9,10,11,11a,12-octahydro-4-oxopyrazino[1',2':4,5][1,4]oxazino[3,2-h]quinoline-3-carboxylic acid.

5. A method of treating bacterial infections which comprises administering to a host requiring such treatment an antibacterially effective amount of a compound of the formula

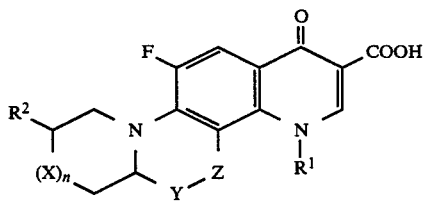

wherein
n is the integer 1 or 0,
X is a group N—R,
R is a hydrogen, $C_{1-4}$-alkyl, $C_{2-4}$-alkylene-N($R^a$, $R^b$), benzyl or benzyl independently ring-substituted by up to 3 substituents selected from the group consisting of hydroxy, halogen, $C_{1-4}$-alkyl, $C_{1-4}$-alkoxy or nitro,
Y is methylene or ethylene,
Z is methylene, O or S,
$R^1$ is $C_{3-6}$-cycloalkyl, N($R^c$, $R^d$), phenyl or phenyl independently substituted by up to 3 substituents selected from the group consisting of hydroxy, halogen, $C_{1-4}$-alkyl, $C_{1-4}$-alkoxy or nitro; or optionally fluorinated $C_{1-4}$-alkyl or $C_{2-4}$-alkenyl,
$R^2$ is hydrogen, $C_{1-4}$-alkyl or, when n is O, it can also be OH or N($R^e$, $R^f$),
$R^a$ to $R^g$ are hydrogen or $C_{1-4}$-alkyl or N($R^a$, $R^b$) is a 5- or 6-membered saturated ring which can contain containing an additional heteroatom selected from O or N—$R^g$,
an enantiomer or diastereomer thereof, or pharmaceutically acceptable salt thereof.

6. A method, in accordance with claim 5, wherein n is the integer 1, R is hydrogen, $C_{1-4}$-alkyl or $C_{2-4}$-alkylene-N($R^a$,$R^b$) and $R^2$ is hydrogen.

7. A method, in accordance with claim 6, wherein R is hydrogen, $C_{1-4}$-alkyl, or p-nitrobenzyl.

8. A pharmaceutical composition comprising an antibacterially effective amount of a compound of the formula

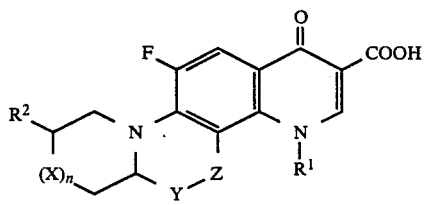

wherein
n is the integer 1 or 0,
X is a group N—R,
R is a hydrogen, $C_{1-4}$-alkyl, $C_{2-4}$-alkylene-N($R^a$, $R^b$), benzyl or benzyl independently ring-substituted by up to 3 substituents selected from the group consisting of hydroxy, halogen, $C_{1-4}$-alkyl, $C_{1-4}$-alkoxy or nitro,
Y is methylene or ethylene,
Z is methylene, O or S,
$R^1$ is $C_{3-6}$-cycloalkyl, N($R^c$, $R^d$), phenyl or phenyl independently substituted by up to 3 substituents selected from the group consisting of hydroxy, halogen, $C_{1-4}$-alkyl, $C_{1-4}$-alkoxy or nitro; or optionally fluorinated $C_{1-4}$-alkyl or $C_{2-4}$-alkenyl,
$R^2$ is hydrogen, $C_{1-4}$-alkyl or, when n is O, it can also be OH or N($R^e$, $R^f$),
$R^a$ to $R^g$ are hydrogen or $C_{1-4}$-alkyl or N($R^a$, $R^b$) is a 5- or 6-membered saturated ring which can contain an additional heteroatom selected from O or N—$R^g$,
an enantiomer or diastereomer thereof, or pharmaceutically acceptable salt thereof, and an inert carrier material.

9. A pharmaceutical composition, in accordance with claim 8, wherein n is the integer 1, R is hydrogen, $C_{1-4}$-alkyl or $C_{2-4}$-alkylene-N($R^a$,$R^b$) and $R^2$ is hydrogen.

10. A pharmaceutical composition, in accordance with claim 8, wherein R is hydrogen, $C_{1-4}$-alkyl or p-nitrobenzyl.

* * * * *